(12) United States Patent
Kong

(10) Patent No.: US 9,406,330 B1
(45) Date of Patent: Aug. 2, 2016

(54) METHOD FOR HDD DISK DEFECT SOURCE DETECTION

(71) Applicant: WD Media, LLC, San Jose, CA (US)

(72) Inventor: Chee Chuan Kong, Penang (MY)

(73) Assignee: WD Media, LLC, San Jose, CA (US)

( * ) Notice: Subject to any disclaimer, the term of this patent is extended or adjusted under 35 U.S.C. 154(b) by 187 days.

(21) Appl. No.: 13/946,972

(22) Filed: Jul. 19, 2013

Related U.S. Application Data

(60) Provisional application No. 61/836,725, filed on Jun. 19, 2013.

(51) Int. Cl.
| | |
|---|---|
| G11B 5/84 | (2006.01) |
| G06T 7/00 | (2006.01) |
| H01L 21/66 | (2006.01) |
| G01N 15/14 | (2006.01) |
| G01N 15/00 | (2006.01) |

(52) U.S. Cl.
CPC .............. *G11B 5/84* (2013.01); *G01N 15/1456* (2013.01); *G06T 7/0008* (2013.01); *H01L 22/20* (2013.01); *G01N 2015/0092* (2013.01)

(58) Field of Classification Search
None
See application file for complete search history.

(56) References Cited

U.S. PATENT DOCUMENTS

| | | | |
|---|---|---|---|
| 5,760,892 A * | 6/1998 | Koyama | G01R 31/311 356/237.1 |
| 5,909,276 A * | 6/1999 | Kinney et al. | 356/237.2 |
| 5,971,586 A * | 10/1999 | Mori | 700/108 |
| 6,013,161 A | 1/2000 | Chen et al. | |
| 6,031,615 A | 2/2000 | Meeks et al. | |
| 6,063,248 A | 5/2000 | Bourez et al. | |
| 6,068,891 A | 5/2000 | O'Dell et al. | |
| 6,086,730 A | 7/2000 | Liu et al. | |
| 6,099,981 A | 8/2000 | Nishimori | |
| 6,103,404 A | 8/2000 | Ross et al. | |
| 6,117,499 A | 9/2000 | Wong et al. | |
| 6,136,403 A | 10/2000 | Prabhakara et al. | |
| 6,143,375 A | 11/2000 | Ross et al. | |
| 6,145,849 A | 11/2000 | Bae et al. | |
| 6,146,737 A | 11/2000 | Malhotra et al. | |
| 6,149,696 A | 11/2000 | Jia | |
| 6,150,015 A | 11/2000 | Bertero et al. | |
| 6,156,404 A | 12/2000 | Ross et al. | |
| 6,159,076 A | 12/2000 | Sun et al. | |
| 6,164,118 A | 12/2000 | Suzuki et al. | |
| 6,200,441 B1 | 3/2001 | Gornicki et al. | |
| 6,204,660 B1 | 3/2001 | Lee | |
| 6,204,995 B1 | 3/2001 | Hokkyo et al. | |
| 6,206,765 B1 | 3/2001 | Sanders et al. | |
| 6,210,819 B1 | 4/2001 | Lal et al. | |
| 6,216,709 B1 | 4/2001 | Fung et al. | |
| 6,221,119 B1 | 4/2001 | Homola | |
| 6,223,303 B1 | 4/2001 | Billings et al. | |

(Continued)

OTHER PUBLICATIONS

Carl E. Barlow, et al., U.S. Appl. No. 13/762,850, filed Feb. 8, 2013, 18 pages.

*Primary Examiner* — Vu Le
*Assistant Examiner* — Tracy Mangialaschi

(57) ABSTRACT

Systems and methods for defect source detection in HDD are provided. The system may include one or more disk processing stations, a disk, a disk defector detector, and a disk defect source detector. This system may be provided in a disk manufacturing environment. The disk defect source detector may be configured to identify a processing station as a source of disk defects by overlaying a disk defect image with a station defect pattern image.

15 Claims, 9 Drawing Sheets

(56) References Cited

U.S. PATENT DOCUMENTS

| | | |
|---|---|---|
| 6,248,395 B1 | 6/2001 | Homola et al. |
| 6,261,681 B1 | 7/2001 | Suekane et al. |
| 6,270,885 B1 | 8/2001 | Hokkyo et al. |
| 6,274,063 B1 | 8/2001 | Li et al. |
| 6,281,676 B1 | 8/2001 | Ottesen et al. |
| 6,283,838 B1 | 9/2001 | Blake et al. |
| 6,287,429 B1 | 9/2001 | Moroishi et al. |
| 6,290,573 B1 | 9/2001 | Suzuki |
| 6,299,947 B1 | 10/2001 | Suzuki et al. |
| 6,303,217 B1 | 10/2001 | Malhotra et al. |
| 6,309,765 B1 | 10/2001 | Suekane et al. |
| 6,358,636 B1 | 3/2002 | Yang et al. |
| 6,362,452 B1 | 3/2002 | Suzuki et al. |
| 6,363,599 B1 | 4/2002 | Bajorek |
| 6,365,012 B1 | 4/2002 | Sato et al. |
| 6,381,090 B1 | 4/2002 | Suzuki et al. |
| 6,381,092 B1 | 4/2002 | Suzuki |
| 6,387,483 B1 | 5/2002 | Hokkyo et al. |
| 6,391,213 B1 | 5/2002 | Homola |
| 6,395,349 B1 | 5/2002 | Salamon |
| 6,403,919 B1 | 6/2002 | Salamon |
| 6,408,677 B1 | 6/2002 | Suzuki |
| 6,426,157 B1 | 7/2002 | Hokkyo et al. |
| 6,429,984 B1 | 8/2002 | Alex |
| 6,482,330 B1 | 11/2002 | Bajorek |
| 6,482,505 B1 | 11/2002 | Bertero et al. |
| 6,500,567 B1 | 12/2002 | Bertero et al. |
| 6,528,124 B1 | 3/2003 | Nguyen |
| 6,548,821 B1 | 4/2003 | Treves et al. |
| 6,552,871 B2 | 4/2003 | Suzuki et al. |
| 6,565,719 B1 | 5/2003 | Lairson et al. |
| 6,566,674 B1 | 5/2003 | Treves et al. |
| 6,571,806 B2 | 6/2003 | Rosano et al. |
| 6,628,466 B2 | 9/2003 | Alex |
| 6,664,503 B1 | 12/2003 | Hsieh et al. |
| 6,670,055 B2 | 12/2003 | Tomiyasu et al. |
| 6,682,807 B2 | 1/2004 | Lairson et al. |
| 6,683,754 B2 | 1/2004 | Suzuki et al. |
| 6,730,420 B1 | 5/2004 | Bertero et al. |
| 6,743,528 B2 | 6/2004 | Suekane et al. |
| 6,759,138 B2 | 7/2004 | Tomiyasu et al. |
| 6,778,353 B1 | 8/2004 | Harper |
| 6,795,274 B1 | 9/2004 | Hsieh et al. |
| 6,855,232 B2 | 2/2005 | Jairson et al. |
| 6,857,937 B2 | 2/2005 | Bajorek |
| 6,862,150 B1 | 3/2005 | Eto |
| 6,876,445 B2 | 4/2005 | Shibuya et al. |
| 6,893,748 B2 | 5/2005 | Bertero et al. |
| 6,899,959 B2 | 5/2005 | Bertero et al. |
| 6,916,558 B2 | 7/2005 | Umezawa et al. |
| 6,939,120 B1 | 9/2005 | Harper |
| 6,946,191 B2 | 9/2005 | Morikawa et al. |
| 6,967,798 B2 | 11/2005 | Homola et al. |
| 6,972,135 B2 | 12/2005 | Homola |
| 6,985,319 B2 | 1/2006 | Yip et al. |
| 7,004,827 B1 | 2/2006 | Suzuki et al. |
| 7,006,323 B1 | 2/2006 | Suzuki |
| 7,016,154 B2 | 3/2006 | Nishihira |
| 7,019,924 B2 | 3/2006 | McNeil et al. |
| 7,045,215 B2 | 5/2006 | Shimokawa |
| 7,070,870 B2 | 7/2006 | Bertero et al. |
| 7,072,129 B1 | 7/2006 | Cullen et al. |
| 7,090,934 B2 | 8/2006 | Hokkyo et al. |
| 7,099,112 B1 | 8/2006 | Harper |
| 7,105,241 B2 | 9/2006 | Shimokawa et al. |
| 7,119,990 B2 | 10/2006 | Bajorek et al. |
| 7,139,145 B1 | 11/2006 | Archibald et al. |
| 7,147,790 B2 | 12/2006 | Wachenschwanz et al. |
| 7,161,753 B2 | 1/2007 | Wachenschwanz et al. |
| 7,166,319 B2 | 1/2007 | Ishiyama |
| 7,166,374 B2 | 1/2007 | Suekane et al. |
| 7,169,487 B2 | 1/2007 | Kawai et al. |
| 7,174,775 B2 | 2/2007 | Ishiyama |
| 7,179,549 B2 | 2/2007 | Malhotra et al. |
| 7,184,139 B2 | 2/2007 | Treves et al. |
| 7,196,860 B2 | 3/2007 | Alex |
| 7,199,977 B2 | 4/2007 | Suzuki et al. |
| 7,206,150 B2 | 4/2007 | Koshkina et al. |
| 7,208,236 B2 | 4/2007 | Morikawa et al. |
| 7,220,500 B1 | 5/2007 | Tomiyasu et al. |
| 7,229,266 B2 | 6/2007 | Harper |
| 7,239,970 B2 | 7/2007 | Treves et al. |
| 7,252,897 B2 | 8/2007 | Shimokawa et al. |
| 7,277,254 B2 | 10/2007 | Shimokawa et al. |
| 7,281,920 B2 | 10/2007 | Homola et al. |
| 7,292,329 B2 | 11/2007 | Treves et al. |
| 7,301,726 B1 | 11/2007 | Suzuki |
| 7,302,148 B2 | 11/2007 | Treves et al. |
| 7,305,119 B2 | 12/2007 | Treves et al. |
| 7,314,404 B2 | 1/2008 | Singh et al. |
| 7,320,584 B1 | 1/2008 | Harper et al. |
| 7,329,114 B2 | 2/2008 | Harper et al. |
| 7,375,362 B2 | 5/2008 | Treves et al. |
| 7,420,886 B2 | 9/2008 | Tomiyasu et al. |
| 7,425,719 B2 | 9/2008 | Treves et al. |
| 7,471,484 B2 | 12/2008 | Wachenschwanz et al. |
| 7,498,062 B2 | 3/2009 | Calcaterra et al. |
| 7,531,485 B2 | 5/2009 | Hara et al. |
| 7,537,846 B2 | 5/2009 | Ishiyama et al. |
| 7,549,209 B2 | 6/2009 | Wachenschwanz et al. |
| 7,569,490 B2 | 8/2009 | Staud |
| 7,583,461 B2 | 9/2009 | Kudoh et al. |
| 7,597,792 B2 | 10/2009 | Homola et al. |
| 7,597,973 B2 | 10/2009 | Ishiyama |
| 7,608,193 B2 | 10/2009 | Wachenschwanz et al. |
| 7,632,087 B2 | 12/2009 | Homola |
| 7,656,615 B2 | 2/2010 | Wachenschwanz et al. |
| 7,682,546 B2 | 3/2010 | Harper |
| 7,684,152 B2 | 3/2010 | Suzuki et al. |
| 7,686,606 B2 | 3/2010 | Harper et al. |
| 7,686,991 B2 | 3/2010 | Harper |
| 7,695,833 B2 | 4/2010 | Ishiyama |
| 7,722,968 B2 | 5/2010 | Ishiyama |
| 7,733,605 B2 | 6/2010 | Suzuki et al. |
| 7,736,768 B2 | 6/2010 | Ishiyama |
| 7,755,861 B1 | 7/2010 | Li et al. |
| 7,758,732 B1 | 7/2010 | Calcaterra et al. |
| 7,833,639 B2 | 11/2010 | Sonobe et al. |
| 7,833,641 B2 | 11/2010 | Tomiyasu et al. |
| 7,834,992 B2 | 11/2010 | Yoshida et al. |
| 7,910,159 B2 | 3/2011 | Jung |
| 7,911,736 B2 | 3/2011 | Bajorek |
| 7,914,845 B2 | 3/2011 | Reiter |
| 7,924,519 B2 | 4/2011 | Lambert |
| 7,944,165 B1 | 5/2011 | O'Dell |
| 7,944,643 B1 | 5/2011 | Jiang et al. |
| 7,952,826 B2 | 5/2011 | Youlian et al. |
| 7,955,723 B2 | 6/2011 | Umezawa et al. |
| 7,983,003 B2 | 7/2011 | Sonobe et al. |
| 7,993,497 B2 | 8/2011 | Moroishi et al. |
| 7,993,765 B2 | 8/2011 | Kim et al. |
| 7,998,912 B2 | 8/2011 | Chen et al. |
| 8,002,901 B1 | 8/2011 | Chen et al. |
| 8,003,237 B2 | 8/2011 | Sonobe et al. |
| 8,012,920 B2 | 9/2011 | Shimokawa |
| 8,038,863 B2 | 10/2011 | Homola |
| 8,045,149 B2 | 10/2011 | Yoshida et al. |
| 8,057,926 B2 | 11/2011 | Ayama et al. |
| 8,062,778 B2 | 11/2011 | Suzuki et al. |
| 8,064,156 B1 | 11/2011 | Suzuki et al. |
| 8,076,013 B2 | 12/2011 | Sonobe et al. |
| 8,092,931 B2 | 1/2012 | Ishiyama et al. |
| 8,094,396 B1 | 1/2012 | Zhang et al. |
| 8,100,685 B1 | 1/2012 | Harper et al. |
| 8,101,054 B2 | 1/2012 | Chen et al. |
| 8,125,723 B1 | 2/2012 | Nichols et al. |
| 8,125,724 B1 | 2/2012 | Nichols et al. |
| 8,137,517 B1 | 3/2012 | Bourez |
| 8,142,916 B2 | 3/2012 | Umezawa et al. |
| 8,163,093 B1 | 4/2012 | Chen et al. |
| 8,169,725 B2 | 5/2012 | Jun |
| 8,171,949 B1 | 5/2012 | Lund et al. |
| 8,173,282 B1 | 5/2012 | Sun et al. |
| 8,178,480 B2 | 5/2012 | Hamakubo et al. |

(56) References Cited

U.S. PATENT DOCUMENTS

| | | |
|---|---|---|
| 8,206,789 B2 | 6/2012 | Suzuki |
| 8,218,260 B2 | 7/2012 | Iamratanakul et al. |
| 8,247,095 B2 | 8/2012 | Champion et al. |
| 8,257,783 B2 | 9/2012 | Suzuki et al. |
| 8,298,609 B1 | 10/2012 | Liew et al. |
| 8,298,689 B2 | 10/2012 | Sonobe et al. |
| 8,306,312 B2 | 11/2012 | Shibuya et al. |
| 8,309,239 B2 | 11/2012 | Umezawa et al. |
| 8,316,668 B1 | 11/2012 | Chan et al. |
| 8,331,056 B2 | 12/2012 | O'Dell |
| 8,354,618 B1 | 1/2013 | Chen et al. |
| 8,367,228 B2 | 2/2013 | Sonobe et al. |
| 8,383,209 B2 | 2/2013 | Ayama |
| 8,394,243 B1 | 3/2013 | Jung et al. |
| 8,397,751 B1 | 3/2013 | Chan et al. |
| 8,399,809 B1 | 3/2013 | Bourez |
| 8,402,638 B1 | 3/2013 | Treves et al. |
| 8,404,056 B1 | 3/2013 | Chen et al. |
| 8,404,369 B2 | 3/2013 | Ruffini et al. |
| 8,404,370 B2 | 3/2013 | Sato et al. |
| 8,406,918 B2 | 3/2013 | Tan et al. |
| 8,414,966 B2 | 4/2013 | Yasumori et al. |
| 8,425,975 B2 | 4/2013 | Ishiyama |
| 8,431,257 B2 | 4/2013 | Kim et al. |
| 8,431,258 B2 | 4/2013 | Onoue et al. |
| 8,453,315 B2 | 6/2013 | Kajiwara et al. |
| 8,488,276 B1 | 7/2013 | Jung et al. |
| 8,491,800 B1 | 7/2013 | Dorsey |
| 8,492,009 B1 | 7/2013 | Homola et al. |
| 8,492,011 B2 | 7/2013 | Itoh et al. |
| 8,493,681 B1 | 7/2013 | Selvaraj |
| 8,496,466 B1 | 7/2013 | Treves et al. |
| 8,517,364 B1 | 8/2013 | Crumley et al. |
| 8,517,657 B2 | 8/2013 | Chen et al. |
| 8,524,052 B1 | 9/2013 | Tan et al. |
| 8,530,065 B1 | 9/2013 | Chernyshov et al. |
| 8,546,000 B2 | 10/2013 | Umezawa |
| 8,551,253 B2 | 10/2013 | Na'im et al. |
| 8,551,627 B2 | 10/2013 | Shimada et al. |
| 8,556,566 B1 | 10/2013 | Suzuki et al. |
| 8,559,131 B2 | 10/2013 | Masuda et al. |
| 8,562,748 B1 | 10/2013 | Chen et al. |
| 8,565,050 B1 | 10/2013 | Bertero et al. |
| 8,570,844 B1 | 10/2013 | Yuan et al. |
| 8,580,410 B2 | 11/2013 | Onoue |
| 8,584,687 B1 | 11/2013 | Chen et al. |
| 8,591,709 B1 | 11/2013 | Lim et al. |
| 8,592,061 B2 | 11/2013 | Onoue et al. |
| 8,596,287 B1 | 12/2013 | Chen et al. |
| 8,597,723 B1 | 12/2013 | Jung et al. |
| 8,603,649 B2 | 12/2013 | Onoue |
| 8,603,650 B2 | 12/2013 | Sonobe et al. |
| 8,605,388 B2 | 12/2013 | Yasumori et al. |
| 8,605,555 B1 | 12/2013 | Chernyshov et al. |
| 8,608,147 B1 | 12/2013 | Yap et al. |
| 8,609,263 B1 | 12/2013 | Chernyshov et al. |
| 8,619,381 B2 | 12/2013 | Moser et al. |
| 8,623,528 B2 | 1/2014 | Umezawa et al. |
| 8,623,529 B2 | 1/2014 | Suzuki |
| 8,634,155 B2 | 1/2014 | Yasumori et al. |
| 8,658,003 B1 | 2/2014 | Bourez |
| 8,658,292 B1 | 2/2014 | Mallary et al. |
| 8,665,541 B2 | 3/2014 | Saito |
| 8,668,953 B1 | 3/2014 | Buechel-Rimmel |
| 8,674,327 B1 | 3/2014 | Poon et al. |
| 8,685,214 B1 | 4/2014 | Moh et al. |
| 8,696,404 B2 | 4/2014 | Sun et al. |
| 8,711,499 B1 | 4/2014 | Desai et al. |
| 8,743,666 B1 | 6/2014 | Bertero et al. |
| 8,758,912 B2 | 6/2014 | Srinivasan et al. |
| 8,787,124 B1 | 7/2014 | Chernyshov et al. |
| 8,787,130 B1 | 7/2014 | Yuan et al. |
| 8,791,391 B2 | 7/2014 | Bourez |
| 8,795,765 B2 | 8/2014 | Koike et al. |
| 8,795,790 B2 | 8/2014 | Sonobe et al. |
| 8,795,857 B2 | 8/2014 | Ayama et al. |
| 8,800,322 B1 | 8/2014 | Chan et al. |
| 8,811,129 B1 | 8/2014 | Yuan et al. |
| 8,817,410 B1 | 8/2014 | Moser et al. |
| 2001/0055172 A1 | 12/2001 | Yip et al. |
| 2002/0060883 A1 | 5/2002 | Suzuki |
| 2002/0181133 A1 | 12/2002 | Koshkina et al. |
| 2002/0191319 A1 | 12/2002 | Liew et al. |
| 2003/0022024 A1 | 1/2003 | Wachenschwanz |
| 2003/0054573 A1* | 3/2003 | Tanaka ............ H01L 21/67276 438/4 |
| 2004/0022387 A1 | 2/2004 | Weikle |
| 2004/0132301 A1 | 7/2004 | Harper et al. |
| 2004/0202793 A1 | 10/2004 | Harper et al. |
| 2004/0202865 A1 | 10/2004 | Homola et al. |
| 2004/0209123 A1 | 10/2004 | Bajorek et al. |
| 2004/0209470 A1 | 10/2004 | Bajorek |
| 2004/0246476 A1* | 12/2004 | Bevis et al. ................ 356/237.5 |
| 2005/0036223 A1 | 2/2005 | Wachenschwanz et al. |
| 2005/0065739 A1* | 3/2005 | Knoch et al. .................... 702/30 |
| 2005/0142990 A1 | 6/2005 | Homola |
| 2005/0150862 A1 | 7/2005 | Harper et al. |
| 2005/0151282 A1 | 7/2005 | Harper et al. |
| 2005/0151283 A1 | 7/2005 | Bajorek et al. |
| 2005/0151300 A1 | 7/2005 | Harper et al. |
| 2005/0155554 A1 | 7/2005 | Saito |
| 2005/0167867 A1 | 8/2005 | Bajorek et al. |
| 2005/0263401 A1 | 12/2005 | Olsen et al. |
| 2006/0056088 A1 | 3/2006 | Kudoh et al. |
| 2006/0147758 A1 | 7/2006 | Jung et al. |
| 2006/0181697 A1 | 8/2006 | Treves et al. |
| 2006/0207890 A1 | 9/2006 | Staud |
| 2007/0070549 A1 | 3/2007 | Suzuki et al. |
| 2007/0146921 A1 | 6/2007 | Jun |
| 2007/0236689 A1 | 10/2007 | Yoshida et al. |
| 2007/0245909 A1 | 10/2007 | Homola |
| 2008/0075845 A1 | 3/2008 | Sonobe et al. |
| 2008/0093760 A1 | 4/2008 | Harper et al. |
| 2009/0117408 A1 | 5/2009 | Umezawa et al. |
| 2009/0136784 A1 | 5/2009 | Suzuki et al. |
| 2009/0169922 A1 | 7/2009 | Ishiyama |
| 2009/0191331 A1 | 7/2009 | Umezawa et al. |
| 2009/0202866 A1 | 8/2009 | Kim et al. |
| 2009/0304259 A1* | 12/2009 | Yamamoto ............ G06T 7/0004 382/145 |
| 2009/0311557 A1 | 12/2009 | Onoue et al. |
| 2010/0143752 A1 | 6/2010 | Ishibashi et al. |
| 2010/0190035 A1 | 7/2010 | Sonobe et al. |
| 2010/0196619 A1 | 8/2010 | Ishiyama |
| 2010/0196740 A1 | 8/2010 | Ayama et al. |
| 2010/0209601 A1 | 8/2010 | Shimokawa et al. |
| 2010/0215992 A1 | 8/2010 | Horikawa et al. |
| 2010/0232065 A1 | 9/2010 | Suzuki et al. |
| 2010/0247965 A1 | 9/2010 | Onoue |
| 2010/0261039 A1 | 10/2010 | Itoh et al. |
| 2010/0269023 A1 | 10/2010 | Yang et al. |
| 2010/0279151 A1 | 11/2010 | Sakamoto et al. |
| 2010/0300884 A1 | 12/2010 | Homola et al. |
| 2010/0304186 A1 | 12/2010 | Shimokawa |
| 2011/0097603 A1 | 4/2011 | Onoue |
| 2011/0097604 A1 | 4/2011 | Onoue |
| 2011/0171495 A1 | 7/2011 | Tachibana et al. |
| 2011/0206947 A1 | 8/2011 | Tachibana et al. |
| 2011/0212346 A1 | 9/2011 | Onoue et al. |
| 2011/0223446 A1 | 9/2011 | Onoue et al. |
| 2011/0244119 A1 | 10/2011 | Umezawa et al. |
| 2011/0299194 A1 | 12/2011 | Aniya et al. |
| 2011/0311841 A1 | 12/2011 | Saito et al. |
| 2012/0069466 A1 | 3/2012 | Okamoto et al. |
| 2012/0070692 A1 | 3/2012 | Sato et al. |
| 2012/0077060 A1 | 3/2012 | Ozawa |
| 2012/0127599 A1 | 5/2012 | Shimokawa et al. |
| 2012/0127601 A1 | 5/2012 | Suzuki et al. |
| 2012/0129009 A1 | 5/2012 | Sato et al. |
| 2012/0140359 A1 | 6/2012 | Tachibana |
| 2012/0141833 A1 | 6/2012 | Umezawa et al. |
| 2012/0141835 A1 | 6/2012 | Sakamoto |
| 2012/0148875 A1 | 6/2012 | Hamakubo et al. |
| 2012/0156523 A1 | 6/2012 | Seki et al. |

(56) References Cited

U.S. PATENT DOCUMENTS

| | | |
|---|---|---|
| 2012/0164488 A1 | 6/2012 | Shin et al. |
| 2012/0170152 A1 | 7/2012 | Sonobe et al. |
| 2012/0171369 A1 | 7/2012 | Koike et al. |
| 2012/0175243 A1 | 7/2012 | Fukuura et al. |
| 2012/0189872 A1 | 7/2012 | Umezawa et al. |
| 2012/0196049 A1* | 8/2012 | Azuma et al. ................. 427/535 |
| 2012/0207919 A1 | 8/2012 | Sakamoto et al. |
| 2012/0216169 A1* | 8/2012 | Park ................. G01N 21/95607 716/136 |
| 2012/0225217 A1 | 9/2012 | Itoh et al. |
| 2012/0251842 A1 | 10/2012 | Yuan et al. |
| 2012/0251846 A1 | 10/2012 | Desai et al. |
| 2012/0276417 A1 | 11/2012 | Shimokawa et al. |
| 2012/0308722 A1 | 12/2012 | Suzuki et al. |
| 2013/0040167 A1 | 2/2013 | Alagarsamy et al. |
| 2013/0071694 A1 | 3/2013 | Srinivasan et al. |
| 2013/0165029 A1 | 6/2013 | Sun et al. |
| 2013/0175252 A1 | 7/2013 | Bourez |
| 2013/0216865 A1 | 8/2013 | Yasumori et al. |
| 2013/0230647 A1 | 9/2013 | Onoue et al. |
| 2013/0314815 A1 | 11/2013 | Yuan et al. |
| 2014/0011054 A1 | 1/2014 | Suzuki |
| 2014/0044992 A1 | 2/2014 | Onoue |
| 2014/0050843 A1 | 2/2014 | Yi et al. |
| 2014/0151360 A1 | 6/2014 | Gregory et al. |
| 2014/0234666 A1 | 8/2014 | Knigge et al. |

* cited by examiner

METHOD FOR HDD DISK DEFECT SOURCE DETECTION

CROSS-REFERENCE TO RELATED APPLICATION

This application claims the benefit of U.S. Provisional Application Ser. No. 61/836,725, filed Jun. 19, 2013, the entire contents of which are herein incorporated by reference as if fully set forth herein.

TECHNICAL FIELD

This invention relates to the field of magnetic media technology, and more specifically, to defect source detection for hard disk drive ("HDD") disks.

BACKGROUND

A HDD disk (or platter) is the magnetic storage medium on which data is stored on the HDD. User-accessible information is magnetically recorded on the magnetic surface of a HDD disk in disk sectors, the smallest size of controllable data in a HDD. Defects or defect patterns may arise on the surface of the disk as it is processed and handled by a plurality of processing stations during manufacture of the disk For example, disk defects can be water stains caused by water in the groove in an insufficiently dried cassette. The stain can be caused by any one of the grooves of the cassette.

Quickly determining the processing station or stations responsible for disk defects is desirable, particularly during yield crisis periods. Current methods of identifying the source (processing station) of disk defects can be time-consuming and not easily adaptable to the different processing stations. For example, in one existing process for detecting whether sputter pins cause defects in a disk, the disk needs to be rescanned using an Optical Surface Analyzer (OSA) to identify the sputter pin location. The OSA scan can then be compared with an existing map of the disk's defects to determine if the sputter pins caused defects on the disk's surface. This existing process may take over an hour and is only adapted to detect sputter pin defects.

BRIEF DESCRIPTION OF THE DRAWINGS

The present application is illustrated by way of example, and not limitation, in the figures of the accompanying drawings in which.

DETAILED DESCRIPTION

In the following description, numerous specific details are set forth to provide a thorough understanding of various embodiment of the present disclosure. It will be apparent to one skilled in the art, however, that these specific details need not be employed to practice various embodiments of the present disclosure. In other instances, well known components or methods have not been described in detail to avoid unnecessarily obscuring various embodiments of the present disclosure.

In accordance with the present disclosure, systems and methods are illustrated for efficiently detecting defect causation on a HDD disk processed through a plurality of processing stations.

Figure 1:
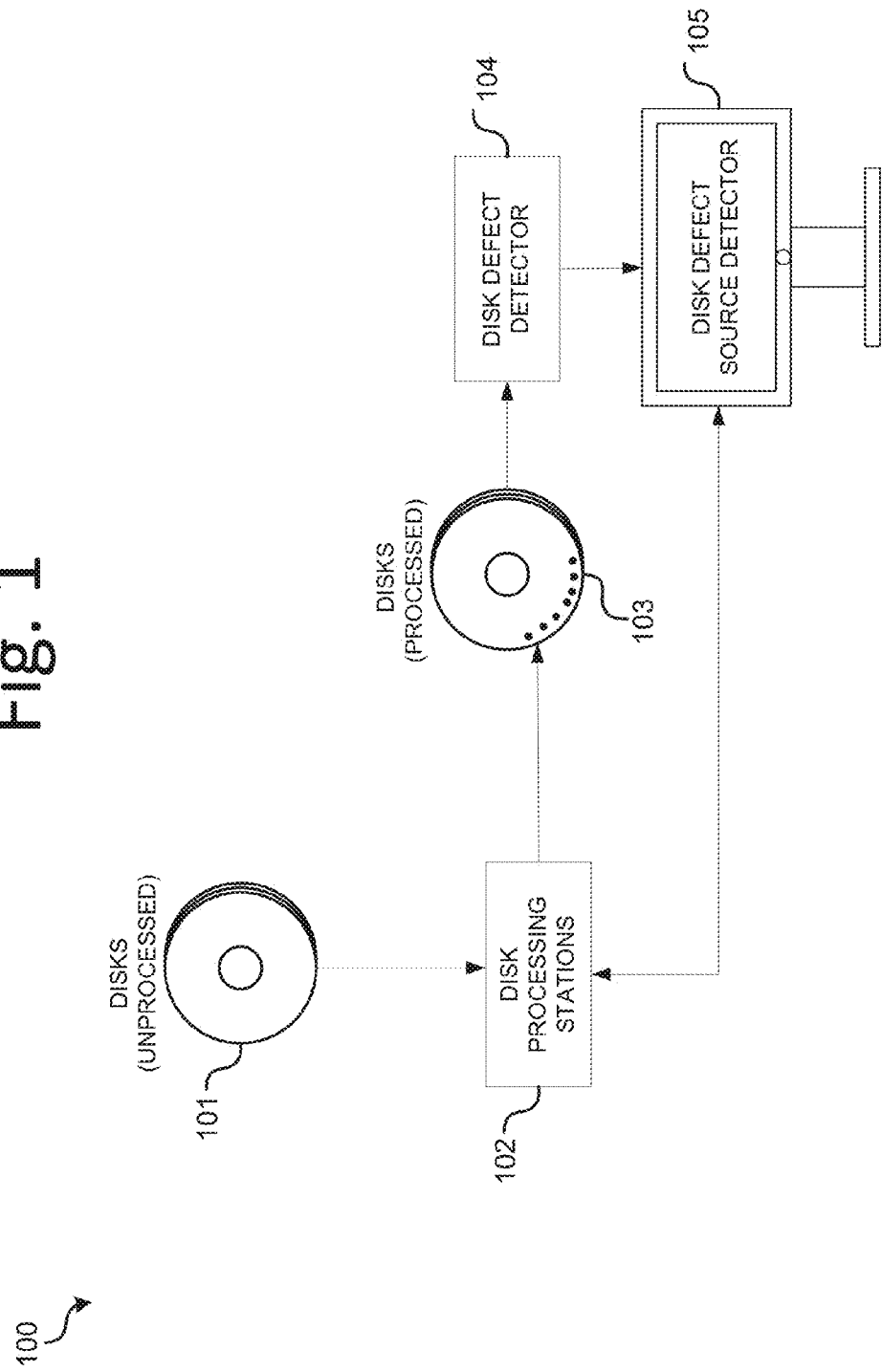
FIG. 1 illustrates a HDD disk processing system in an example disk manufacturing environment in accordance with one embodiment of the technology described herein.

FIG. 1 illustrates a HDD disk processing system in an example disk manufacturing environment in accordance with one embodiment of the technology described herein. Unprocessed disks 101 may be handled by one or more disk processing stations 102 during the manufacture of disks 101. After processing through one or more disk processing stations 102, processed disks 101 may develop surface defects such as scratches, dirt, or water stains because of problems with one or more processing stations 102. A disk defect detector 104 may scan for any surface defects or defect patterns during any processing stage. If defects are detected on processed disks 103, disk defect source detector 105 may be used to determine the cause of the defects, for example, a particular disk processing station 102. The cause of disk defects may then be determined and remedied.

System 100 may be implemented in a single disk manufacturing facility that processes the disks and performs defect testing to determine if there are issues with processed disk 103 or disk processing stations 102. Alternatively, system 100 may be implemented in distributed facilities. For example, in one implementation the processing of disks is handled by one facility (e.g. manufacturing plant) and the defect testing and troubleshooting of processed disks 103 is handled by another facility (e.g. quality control plant). These facilities may be remotely distributed. These facilities may additionally implement additional processes for assembling HDD that include the manufactured disks.

Disk 101 comprises any disk that may serve as a magnetic storage medium in a HDD of any form factor. For example, disk 101 may have a form factor of 65 mm or 95 mm (i.e. 2.5" or 3.5"). Disk 101 may be two-sided (data recordable on both sides). Moreover, disk 101 may be manufactured as part of an assembly of multiple disks in one HDD.

A disk processing station 102 is any machine or tool that contacts the surface of disk 101 during its manufacture. For two-sided disks, disk processing station 102 may contact both surfaces (sides). A disk processing station 102 may be, for example, a sputtering device such as a magnetron sputtering device that deposits a magnetic film on the disk surface. During sputtering, disk 101 may be held in place by two or more sputter pins that contact its surface. As another example, a disk processing station may be a UV saddle for holding a disk in place as it undergoes a UV irradiation process. The UV saddle circumferentially contacts the outer edge of the disk along a circular segment of the disk. Other exemplary disk processing stations 102 may include shipping cassettes, robot paddles, modular clean line combs or modular dryer combs.

Figure 2:
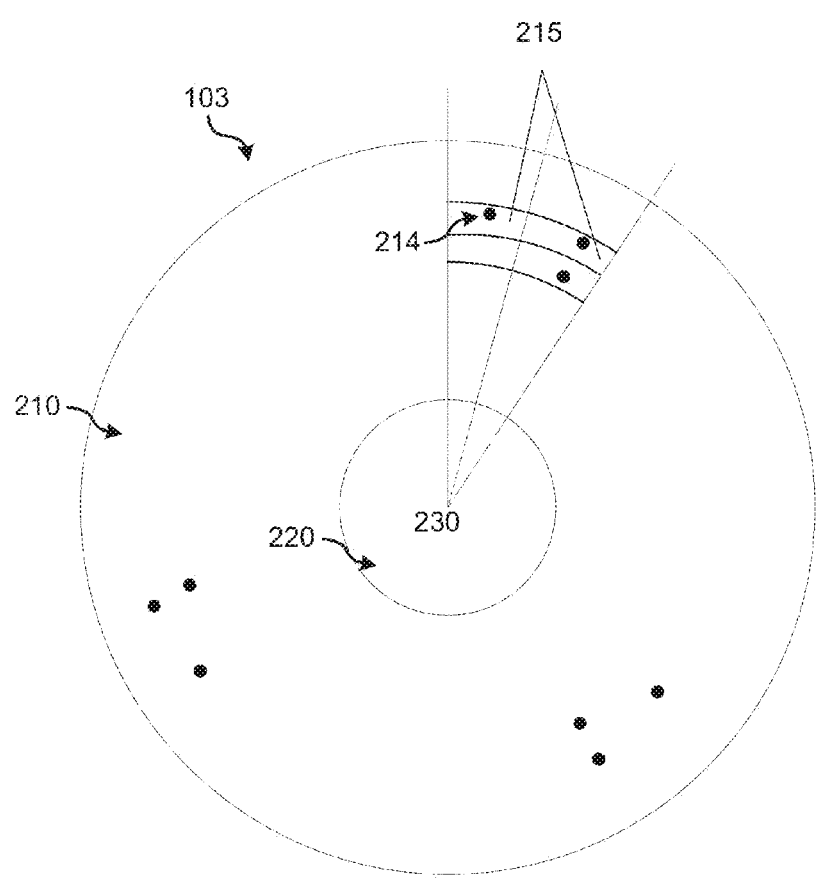
FIG. 2 illustrates an example disk after processing in the system of FIG. 1.

FIG. 2 illustrates an example disk 103 after processing in the system of FIG. 1. Disk 103 comprises an inner region 220 for mounting on a HDD spindle and outer surface region 210 where data may be recorded once the disk has undergone sufficient processes for data recording. In this exemplary illustration, defects 214 formed on the surface of disk 103 because of processing through one or more processing stations 102. A defect 214 is any scratch, stain, contamination, or unwanted surface formation that formed on the surface of disk 103 during processing. As is further described below, defects 214 in the disk sectors 215 of disk 103 may be mapped to a disk defect image.

Disk defects 214 may be caused by the disk surface contact points of disk processing stations 102. For example, disk defects can be scratches or contaminants caused by burrs on the robot paddle that loads the disk into a cassette. In another example, disk defects 214 can be sputter pin voids caused by contaminants on the disk holder pins of the sputter device. In yet another example, disk defects 214 may be water stains caused by water in the groove of an insufficiently dried cassette.

Disk defects 214 may assume a particular pattern because they are caused by a processing station's disk surface 210 contact points. For example, FIG. 2 illustrates three defect sets (each set comprising three defects) that are approximately equidistant and similarly distributed along the surface 210 of disk 103. The illustrated defects, for example, can be caused by a sputter device with three disk holder pins. As is further described below, knowledge of the expected defect pattern for a particular disk processing station 102 may be implemented in a process for quickly identifying the processing station 102 responsible for disk defects 214.

Figure 3:
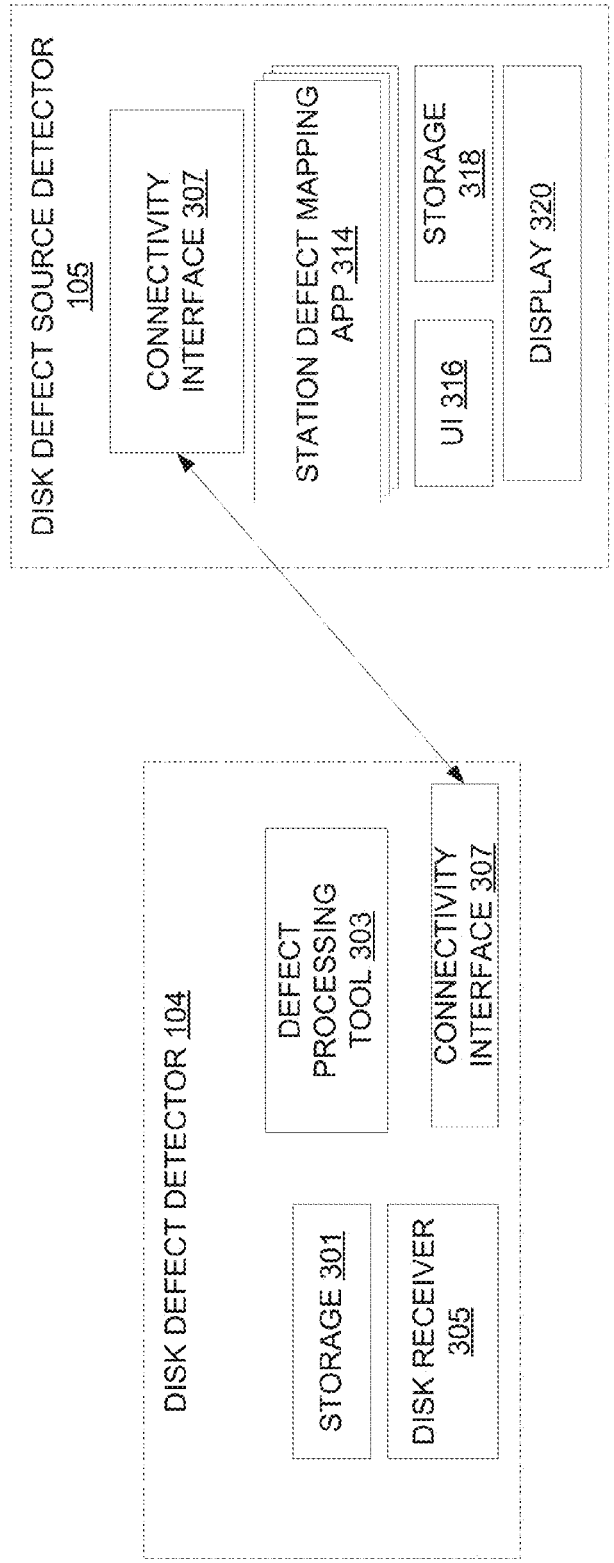
FIG. 3 is a high-level block diagram illustrating an example disk defect detector and troubleshooting device that may be used in the system of FIG. 1.

FIG. 3 is a high-level block diagram illustrating an example disk defect detector 104 and disk defect source detector 105 that may be used in the system of FIG. 1 to detect disk defects and determine their source. Disk defect detector 104 may comprise a storage 301, a disk defect processing tool 303, a disk receiver 305, and connectivity interface 307. Disk receiver 305 may comprise any tool configured to receive a disk for defect testing, for example, any disk defect testing tool with a disk read/write head. Defect processing tool 303 may be used in combination with disk receiver 305 to scan for disk defects. In one implementation, more than one disk defect detector 104 is used to perform disk defect testing. In this implementation, this plurality of disk defect detectors 104 may be integrated as a disk defect detector assembly. The disk defect detector assembly may comprise more than one disk receiver 305 and one or more disk defect processing tools 303.

In this exemplary implementation, defect processing tool 303 scans for defects over all sectors in the disk (entire surface area). In another implementation, defect processing tool 303 may scan for defects over a partial surface area of the disk. If a disk defect is detected, defect processing tool 303 may identify the defect's location on the disk by disk sector identifier, circular sector and radius, disk track number and angle, or any coordinate set (e.g. polar) that may be used to map the disk defect location onto a disk surface image or polar map. The set of identified disk defect locations for a disk may be stored as a single file recorded in storage 301. Alternatively, the set of identified disk defect locations for a disk may be stored as a single file recorded on one or more sectors of the disk. This file (set of identified disk defect locations) may be referred to as a disk defect data set.

Connectivity interface 307 may be included to provide a wired or wireless communications link with disk defect source detector 105 for communicating data such as a disk defect data set for use by one or more applications ran by disk defect source detector 105.

Disk defect source detector 105 may comprise a station defect mapping application 314, a user interface 316, a storage 318, and a display 320. Disk defect source detector 105 may be any hand-held computing device (tablets, PDA's, smartphones, cellphones, palmtops, etc.); workstations or servers; or any other type of computing device configured to run station defect mapping application 314. User interface 316 may be configured to allow user input into station defect mapping application 314 for display on a display 320. In one implementation, troubleshooting device 105 and disk defect detector 104 may be integrated as a single device.

Figure 4:
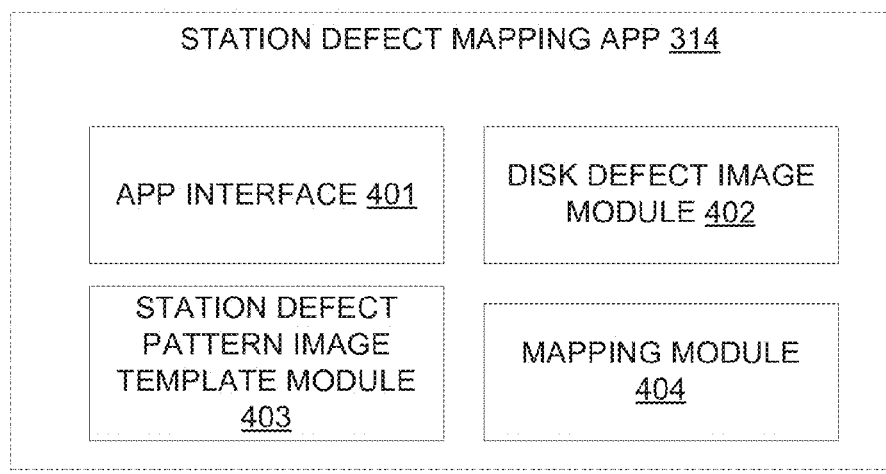
FIG. 4 illustrates an example station defect mapping application for defect source detection in a disk.

FIG. 4 illustrates a station defect mapping application 314 for defect source detection in a disk. Station defect mapping application 314 may comprise an application interface 401, a disk defect image module 402, a station defect image template module 403, and a mapping module 404. These modules may be integrated in any combination. Application interface 401 may allow a user of defect mapping application 314 to interact with the application via user interface 316 and perform operations such as selecting a disk defect data set and other application parameters such as a disk form factor, a graphical coordinate set, and a station defect pattern image (described below). Mapping module 404 may be configured to interact with disk defect image module 402 and station defect pattern image template module 403 to graphically map a disk defect data set and station defect pattern image onto a disk surface image, polar map, or other graphical representation of a disk surface. Together, these modules may allow a user of station defect mapping application 314 to quickly determine a source (processing station) of disk defects.

Figure 5:
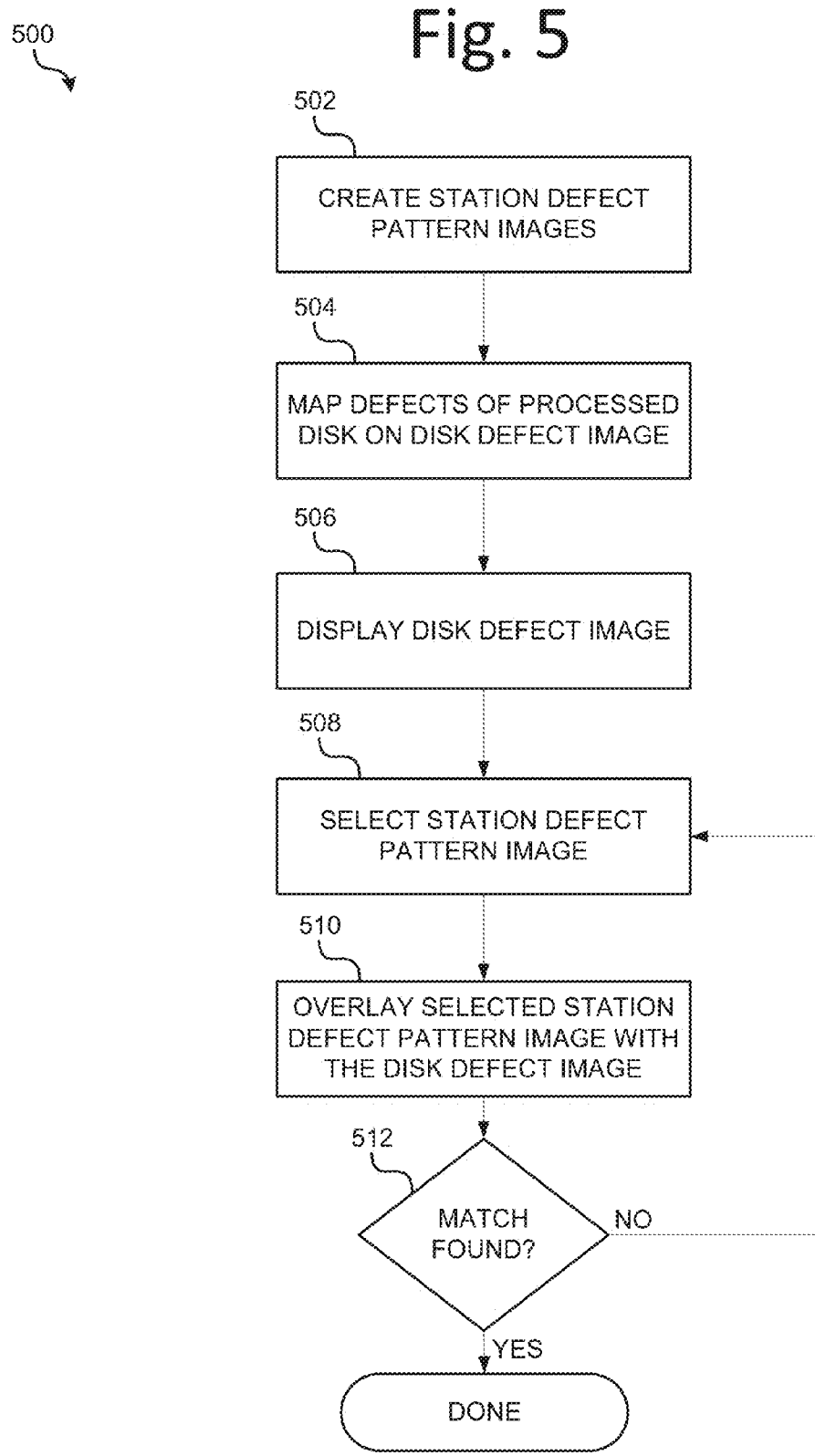
FIG. 5 is an operational flow diagram illustrating an example process used for defect source detection in a disk processed through the system in FIG. 1.

FIG. 5 is an operational flow diagram illustrating an example process 500 used for defect source (disk processing station) detection in a disk processed through the system in FIG. 1. Some or all of the operations in process 500 may be implemented by disk defect source detector 105 using station defect mapping application 314. Alternatively, the operations in process 500 may be implemented by an integrated device comprising disk defect detector 104 and disk defect source detector 105.

At operation 502, one or more station defect pattern images (or station image templates) are created for one or more disk processing stations 102. FIGS. 6A-6D illustrates four exemplary station defect pattern images 610 through 640. A station defect pattern image maps the disk surface contact points of a disk processing station 102 onto a disk surface. As discussed above, these disk surface contact points may cause unwanted surface defects such as scratches, stains, or contamination. A disk surface image 605 may be included in a station defect pattern image for reference. The mapped disk surface contact points may be mapped to scale. Alternatively, the mapped disk surface contact points may not be mapped to scale if, for example, they are used as a template for display on an application user interface to approximately indicate the disk surface area a disk processing station 102 contacts.

Figure 6:
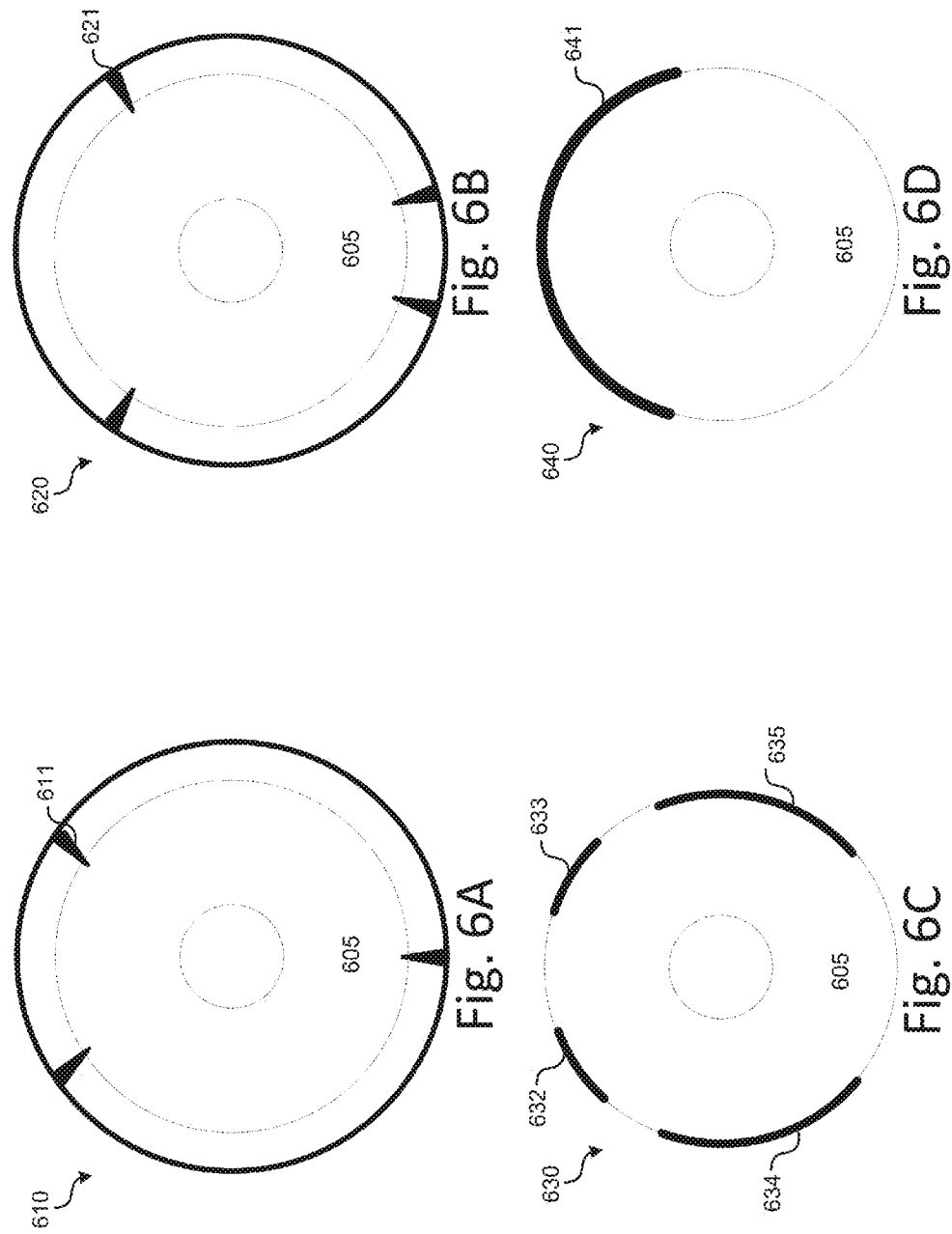
FIGS. 6A-6D illustrates station defect pattern image templates that may be used in the process of FIG. 5.

FIG. 6A illustrates a station defect pattern image 610 for a sputtering device with three pins 611. FIG. 6B illustrates a station defect pattern image 620 for a sputtering device with four pins 621. FIG. 6C illustrates a station defect pattern image 630 for a disk shipping cassette with four disk circumferential contact areas 632 through 635. FIG. 6D illustrates a station defect pattern image 640 for a robot paddle with disk circumferential contact area 640.

In some implementations, a plurality of defect pattern images may be created for a single processing station. For example, each station defect pattern image for a disk processing station may correspond to a different set of contacts points on the processing station. Alternatively, the same contact points on the processing station may produce different station defect patterns depending on the cause of the defects (e.g. dirt obscuring the contact points or wear on the contact points).

After a station defect pattern image is created, it may be added to storage 318 or a memory for reuse by station defect mapping application 314 in disk defect source detector 105. Accordingly, operation 502 may be performed only if station defect pattern images are not available for every disk processing station 102 used to process a disk. As new disk processing stations 102 are added to disk processing system 100, additional station defect pattern images may be dynamically created for use by defect mapping application 314 in disk source detector 105. Thus, system 100 and process 500 are adapted to add new disk processing stations 102.

Figure 7:
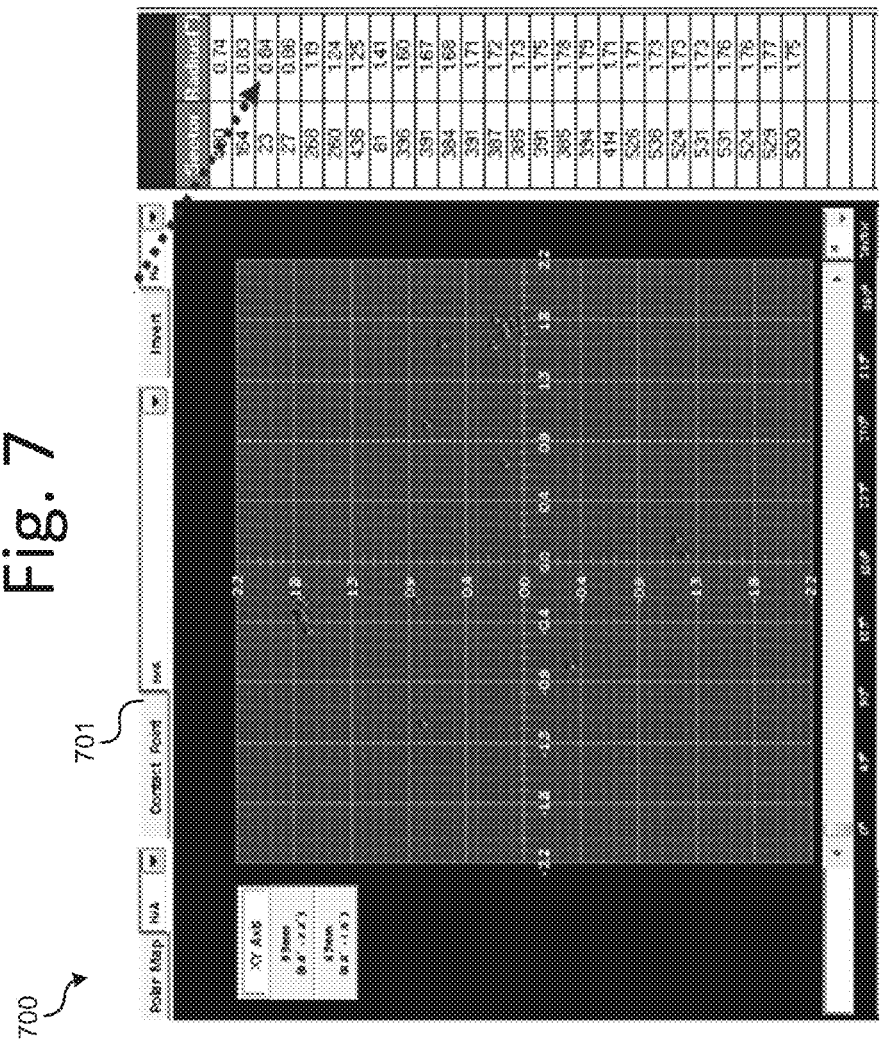
FIG. 7 is a screenshot of an example defect mapping application that may be used in accordance with the process of FIG. 5.

At operation 504, a disk defect data set (i.e. the defects of the processed disk) is mapped onto a disk defect image. At operation 506, the disk defect image may then be displayed on display 320. A disk defect image graphically represents the location of disk surface defects. The disk defect image may be represented, for example, on a polar graph or two-dimensional Cartesian graph. FIG. 7 is a screenshot 700 of an example defect mapping application 701 displaying a disk defect image after operation 506. In this example application, the disk defect image is represented on a polar graph. Example application 701 also displays the disk defect data set used to create the disk defect image. The disk defect data set, in this example, represents each defect location as a circular sector and radius pair.

Figure 8:
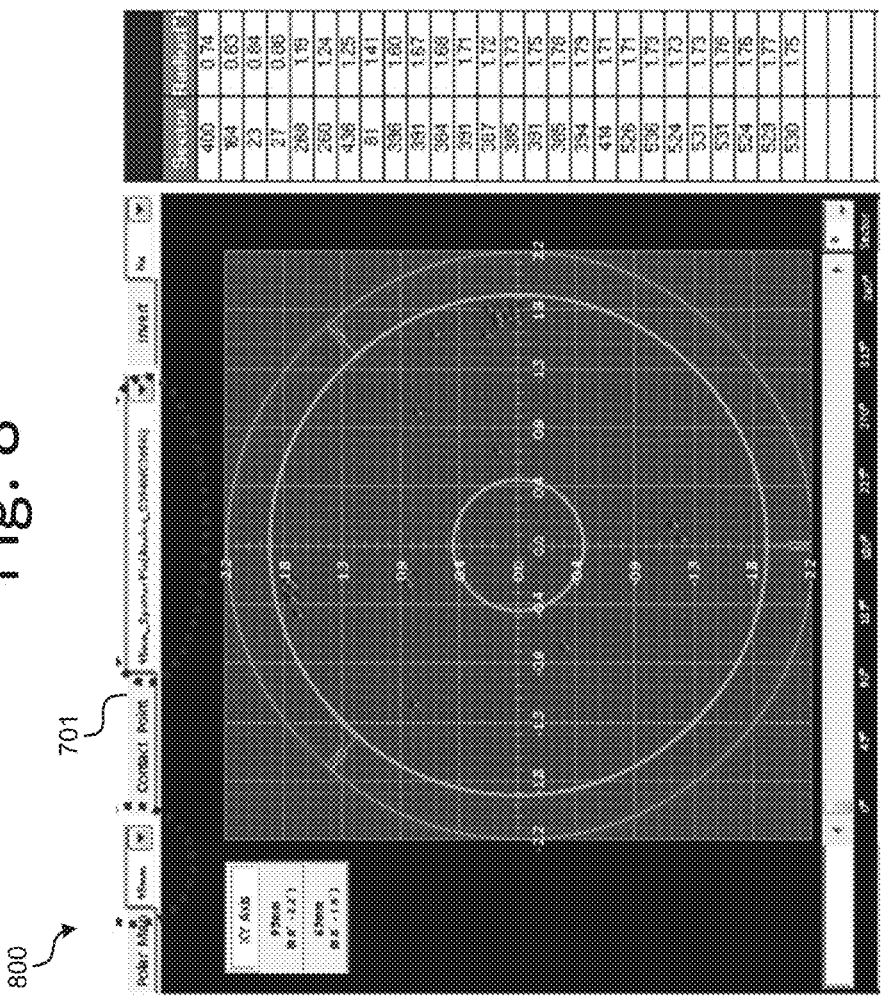
FIG. 8 is another screenshot of an example defect mapping application that may be used in accordance with the process of FIG. 5.

At operation 508, a station defect pattern image is selected. The station defect pattern image may be manually selected by the user of station defect mapping application 314. The selected station defect pattern image may then be overlaid with the disk defect image (operation 510). FIG. 8 is another screenshot 800 of example defect mapping application 701 and illustrates a station defect pattern image overlaid over a disk defect image on a polar graph. In this example application, a three pin sputter device defect patter image is overlaid over a disk defect image. In some implementations, a second station defect pattern image may be simultaneously overlaid over the disk defect image with the first overlaid station defect pattern image.

At operation 512, the overlaid station defect pattern image and disk defect image may be compared to determine if they correspond. The two overlaid images may correspond if the mapped disk defect locations are located on the same disk sector or general disk surface area as the mapped disk processing station disk surface contact points. Because there may be an angular displacement between the two disk-surface (circularly) mapped images, during comparison the disk defect image may be angularly rotated about its center (0 to 360 degrees). Alternatively, the station defect pattern image may be angularly rotated about its center (0 to 360 degrees).

If the overlaid images correspond (i.e. there is a match), then the disk processing station 102 with station defect pattern image has been identified as the source of disk defects. If the two overlaid images do not correspond (i.e. there is no match), operations 508 through 512 may be repeated with other station defect pattern images until a match is found. The degree of correspondence necessary to find a match between the two images may be user defined or predefined by image comparison algorithms.

In some implementations, each operation in process 500 may be performed in response to user input into station defect mapping application 314. Alternatively, some or all of the operations may be automated such that station defect mapping application 314 takes a disk defect data set and automatically compares it with a set of station defect pattern images.

Figure 9:
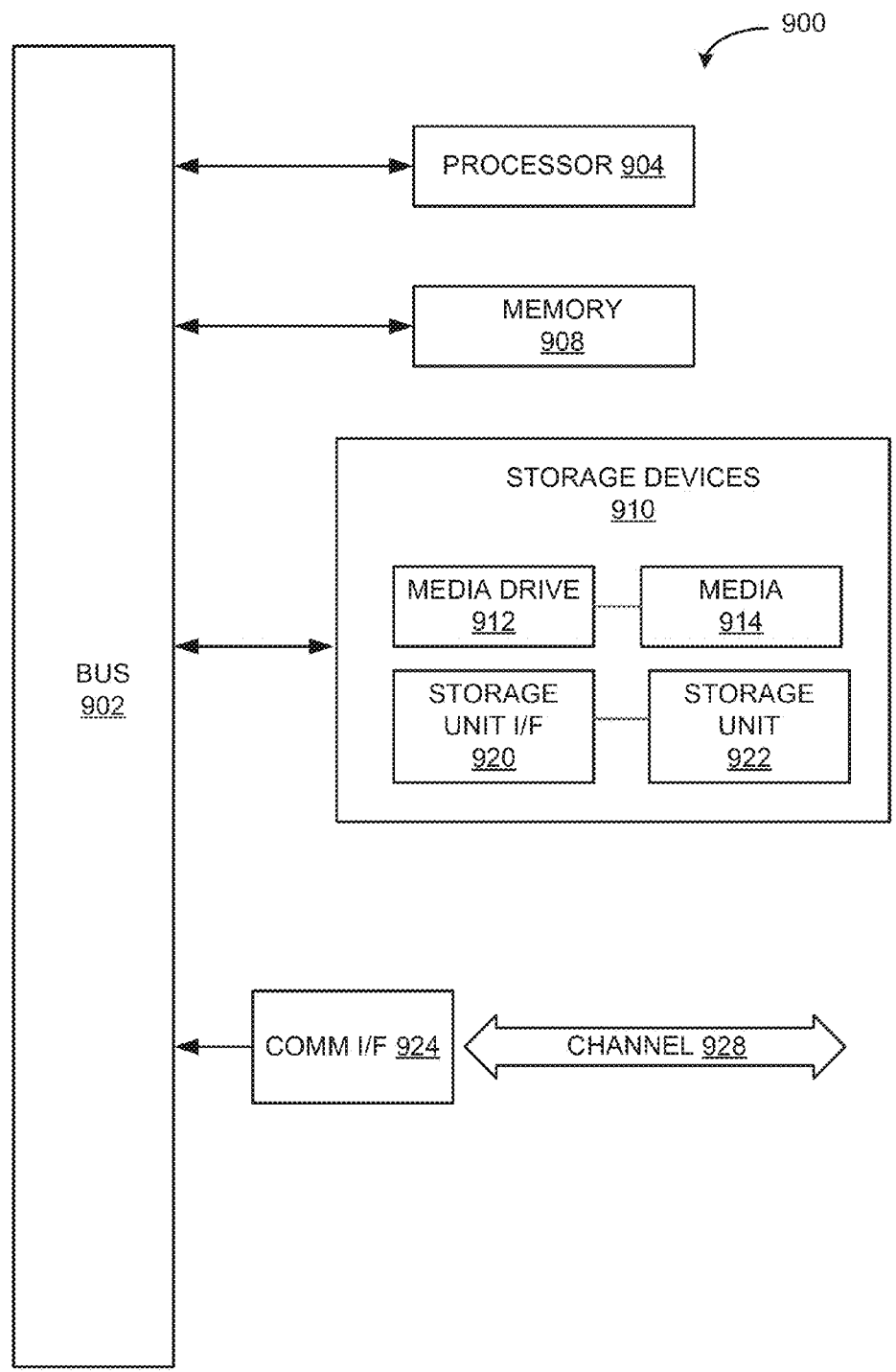
FIG. 9 illustrates an example computing module that may be used to implement various features of the system and methods disclosed herein.

FIG. 9 illustrates an example computing module that may be used to implement various features of the system and methods disclosed herein.

As used herein, the term module might describe a given unit of functionality that can be performed in accordance with one or more embodiments of the present application. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the application are implemented in whole or in part using software, in one embodiment, these software elements can be implemented to operate with a computing or processing module capable of carrying out the functionality described with respect thereto. One such example computing module is shown in FIG. 9. Various embodiments are described in terms of this example-computing module 900. After reading this description, it will become apparent to a person skilled in the relevant art how to implement the application using other computing modules or architectures.

Referring now to FIG. 9, computing module 900 may represent, for example, computing or processing capabilities found within desktop, laptop, notebook, and tablet computers; hand-held computing devices (tablets, PDA's, smart phones, cell phones, palmtops, etc.); mainframes, supercomputers, workstations or servers; or any other type of special-purpose or general-purpose computing devices as may be desirable or appropriate for a given application or environment. Computing module 900 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 900 might include, for example, one or more processors, controllers, control modules, or other processing devices, such as a processor 904. Processor 904 might be implemented using a general-purpose or special-purpose processing engine such as, for example, a microprocessor, controller, or other control logic. In the illustrated example, processor 904 is connected to a bus 902, although any communication medium can be used to facilitate interaction with other components of computing module 900 or to communicate externally.

Computing module 900 might also include one or more memory modules, simply referred to herein as main memory 908. For example, preferably random access memory (RAM) or other dynamic memory, might be used for storing information and instructions to be executed by processor 904. Main memory 908 might also be used for storing temporary variables or other intermediate information during execution of instructions to be executed by processor 904. Computing module 900 might likewise include a read only memory ("ROM") or other static storage device coupled to bus 902 for storing static information and instructions for processor 904.

The computing module 900 might also include one or more various forms of information storage mechanism 910, which might include, for example, a media drive 912 and a storage unit interface 920. The media drive 912 might include a drive or other mechanism to support fixed or removable storage media 914. For example, a hard disk drive, a floppy disk drive, a magnetic tape drive, an optical disk drive, a CD or DVD drive (R or RW), or other removable or fixed media drive might be provided. Accordingly, storage media 914 might include, for example, a hard disk, a floppy disk, magnetic tape, cartridge, optical disk, a CD or DVD, or other fixed or removable medium that is read by, written to or accessed by media drive 912. As these examples illustrate, the storage media 914 can include a computer usable storage medium having stored therein computer software or data.

In alternative embodiments, information storage mechanism 910 might include other similar instrumentalities for allowing computer programs or other instructions or data to be loaded into computing module 900. Such instrumentalities might include, for example, a fixed or removable storage unit 922 and an interface 920. Examples of such storage units 922 and interfaces 920 can include a program cartridge and cartridge interface, a removable memory (for example, a flash memory or other removable memory module) and memory slot, a PCMCIA slot and card, and other fixed or removable storage units 922 and interfaces 920 that allow software and data to be transferred from the storage unit 922 to computing module 900.

Computing module 900 might also include a communications interface 924. Communications interface 924 might be used to allow software and data to be transferred between computing module 900 and external devices. Examples of communications interface 924 might include a modem or soft modem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 924 might typically be carried on signals, which can be electronic, electromagnetic (which includes optical) or other signals capable of being exchanged by a given communications interface 924. These signals might be provided to communications interface 924 via a channel 928. This channel 928 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media such as, for example, memory 908, storage unit 920, media 914, and channel 928. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 900 to perform features or functions of the present application as discussed herein.

Although described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the application, whether or not such embodiments are described and whether or not such features are presented as being a part of a described embodiment. Thus, the breadth and scope of the present application should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:
1. A method for determining defect causation on a magnetic disk, comprising:

creating a first station defect pattern image for a first disk processing station by mapping disk surface areas contacted by the first disk processing station;

creating a second station defect pattern image for a second disk processing station by mapping disk surface areas contacted by the second disk processing station;

after creating the first and second station defect pattern images, mapping defects detected on a processed disk on a disk defect image;

overlaying the first station defect pattern image with the disk defect image;

determining if the first station defect pattern image corresponds to the disk defect image;

overlaying the second station defect pattern image with the disk defect image; and determining if the second station defect pattern image corresponds to the disk defect image.

2. The method of claim 1, further comprising processing the disk through the first and second disk processing stations prior to mapping defects detected on the processed disk.

3. The method of claim 1, wherein determining if the first station defect pattern image corresponds to the disk defect image comprises angularly rotating the overlaid first station defect pattern image about its center.

4. The method of claim 1, wherein each of the first and second processing stations comprises sputter pins, shipping cassettes, robot paddles, UV saddles, modular clean line combs, or modular dryer combs.

5. The method of claim 1, wherein a plurality of first station defect pattern images are created for the first processing station and wherein the plurality of station defect pattern images are overlaid with the disk defect image.

6. The method of claim 5, further comprising determining if any one of the plurality of first station defect pattern images correspond to the disk defect image.

7. The method of claim 1, wherein the disk defect image comprises an image of a plurality of disk defect locations, wherein each disk defect location comprises a circular sector and radius pair.

8. The method of claim 1, wherein the disk form factor is 95 mm or 65 mm.

9. A non-transitory computer readable medium having computer executable program code embodied thereon, the computer executable program code configured to cause a computing device to:

create a first station defect pattern image for a first disk processing station based on a mapping of disk surface areas contacted by the first disk processing station;

create a second station defect pattern image for a second disk processing station based on a mapping of disk surface areas contacted by the second disk processing station;

after creating the first and second station defect pattern images, map defects detected on a processed magnetic disk on a disk defect image;

overlay the first station defect pattern image with the disk defect image;

determine if the first station defect pattern image corresponds to the disk defect image;

overlay the second station defect pattern image with the disk defect image; and determine if the second station defect pattern image corresponds to the disk defect image.

10. The computer readable medium of claim 9, wherein determining if the first station defect pattern image corresponds to the disk defect image comprises angularly rotating the overlaid first station defect pattern image about its center.

11. The computer readable medium of claim 9, wherein each of the first and second processing stations comprises sputter pins, shipping cassettes, robot paddles, UV saddles, modular clean line combs, or modular dryer combs.

12. The computer readable medium of claim 9, wherein a plurality of first station defect pattern images are created for the first processing station and wherein the plurality of first station defect pattern images are overlaid with the disk defect image.

13. The computer readable medium of claim 12, wherein the computer executable program code is further configured to cause a computing device to determine if any one of the plurality of first station defect pattern images correspond to the disk defect image.

14. The computer readable medium of claim 9, wherein the disk defect image comprises an image of a plurality of disk defect locations, wherein each disk defect location comprises a circular sector and radius pair.

15. The computer readable medium of claim 9, wherein the disk form factor is 95 mm or 65 mm.

* * * * *